(12) United States Patent
Hines et al.

(10) Patent No.: US 10,300,009 B2
(45) Date of Patent: May 28, 2019

(54) TOPICAL COSMETIC COMPOSITIONS

(71) Applicant: Mary Kay Inc., Addison, TX (US)

(72) Inventors: Michelle Hines, Hickory Creek, TX (US); Geetha Kalahasti, Plano, TX (US); Tiffany Florence, Dallas, TX (US); David Gan, Southlake, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 15/378,597

(22) Filed: Dec. 14, 2016

(65) Prior Publication Data

US 2017/0172911 A1  Jun. 22, 2017

Related U.S. Application Data

(60) Provisional application No. 62/269,509, filed on Dec. 18, 2015.

(51) Int. Cl.

| | |
|---|---|
| *A61K 36/00* | (2006.01) |
| *A61K 8/97* | (2017.01) |
| *A61K 8/31* | (2006.01) |
| *A61K 8/34* | (2006.01) |
| *A61K 8/37* | (2006.01) |
| *A61K 8/41* | (2006.01) |
| *A61K 8/55* | (2006.01) |
| *A61K 8/67* | (2006.01) |
| *A61K 8/81* | (2006.01) |
| *A61K 8/891* | (2006.01) |
| *A61K 8/895* | (2006.01) |
| *A61K 8/92* | (2006.01) |
| *A61K 9/00* | (2006.01) |
| *A61K 36/33* | (2006.01) |
| *A61Q 19/08* | (2006.01) |
| *A61Q 19/00* | (2006.01) |
| *A61K 8/9789* | (2017.01) |

(52) U.S. Cl.
CPC .................. *A61K 8/97* (2013.01); *A61K 8/31* (2013.01); *A61K 8/342* (2013.01); *A61K 8/345* (2013.01); *A61K 8/37* (2013.01); *A61K 8/375* (2013.01); *A61K 8/41* (2013.01); *A61K 8/55* (2013.01); *A61K 8/673* (2013.01); *A61K 8/8152* (2013.01); *A61K 8/8194* (2013.01); *A61K 8/891* (2013.01); *A61K 8/895* (2013.01); *A61K 8/922* (2013.01); *A61K 8/9789* (2017.08); *A61K 9/0014* (2013.01); *A61K 36/33* (2013.01); *A61Q 19/00* (2013.01); *A61Q 19/08* (2013.01); *A61K 2800/30* (2013.01); *A61K 2800/78* (2013.01); *A61K 2800/782* (2013.01); *A61K 2800/87* (2013.01)

(58) Field of Classification Search
CPC ........................................... A61K 36/00
See application file for complete search history.

(56) References Cited

U.S. PATENT DOCUMENTS

| | | | |
|---|---|---|---|
| 2,798,053 A | 7/1957 | Brown et al. | 521/38 |
| 3,755,560 A | 8/1973 | Dickert et al. | 514/772.6 |
| 4,421,769 A | 12/1983 | Dixon et al. | 514/772 |
| 4,509,949 A | 4/1985 | Huang et al. | 8/558 |
| 4,599,379 A | 7/1986 | Flesher et al. | 524/801 |
| 4,628,078 A | 12/1986 | Glover et al. | 526/303.1 |
| 4,835,206 A | 5/1989 | Farrar et al. | 524/457 |
| 4,849,484 A | 7/1989 | Heard | 525/221 |
| 5,011,681 A | 4/1991 | Ciotti et al. | 510/136 |
| 5,087,445 A | 2/1992 | Haffey et al. | 424/78.35 |
| 5,100,660 A | 3/1992 | Hawe et al. | 424/78.35 |
| 5,736,584 A | 4/1998 | Kunkel | 424/767 |
| 6,447,820 B1 | 9/2002 | Niazi | 424/767 |
| 6,649,178 B2 | 11/2003 | Mohammadi et al. | 424/401 |
| 6,737,086 B2 | 5/2004 | Gutierrez et al. | 424/767 |
| 7,344,728 B1 | 3/2008 | Perry | 424/406 |
| 7,722,904 B2 | 5/2010 | Schneider et al. | 424/746 |
| 7,999,008 B2 | 8/2011 | Bernard et al. | 514/588 |
| 8,455,013 B2 | 6/2013 | Dumas et al. | 424/725 |
| 2004/0109905 A1 | 6/2004 | Bagchi | 424/732 |
| 2005/0013871 A1 | 1/2005 | Niazi et al. | 424/539 |
| 2005/0163880 A1 | 7/2005 | Pusateri et al. | 424/777 |
| 2005/0196373 A1 | 9/2005 | Chen | 424/74 |
| 2007/0141186 A1* | 6/2007 | Shin | A23L 2/04 424/767 |
| 2008/0119527 A1 | 5/2008 | Baldo | 514/355 |
| 2008/0199489 A1 | 8/2008 | Parrinello | 424/195.17 |
| 2008/0261916 A1 | 10/2008 | Jaszberenyi et al. | 514/58 |

(Continued)

FOREIGN PATENT DOCUMENTS

| | | | | |
|---|---|---|---|---|
| DE | 202006019113 U1 | * | 2/2007 | ........... A61K 36/185 |
| KR | 2003023398 A | * | 3/2003 | |

(Continued)

OTHER PUBLICATIONS

Written Opinion issued in International Patent Application No. PCT/US2016/066567 dated Apr. 26, 2017.

International Search Report and Written Opinion issued in Application No. PCT/US2016/066567, dated Apr. 26, 2017.

(Continued)

*Primary Examiner* — Qiuwen Mi

(74) *Attorney, Agent, or Firm* — Norton Rose Fulbright US LLP

(57) ABSTRACT

Disclosed are compositions and methods for their use for reducing tumor necrosis factor alpha (TNF-α) and/or vascular endothelial growth factor (VEGF) production in skin cells by topically applying to skin in need thereof, a composition comprising an effective amount of *Opuntia ficus-indica tuna*, *Opuntia ficus-indica nopales*, or both, or extracts thereof, to reduce TNF-α or VEGF production in skin cells.

11 Claims, No Drawings

(56) References Cited

U.S. PATENT DOCUMENTS

| | | |
|---|---|---|
| 2008/0268547 A1 | 10/2008 | Avent et al. .................. 436/164 |
| 2009/0035294 A1 | 2/2009 | Mahe et al. ................ 424/94.63 |
| 2009/0117211 A1 | 5/2009 | Schneider et al. ............ 424/747 |
| 2009/0252796 A1 | 10/2009 | Mazed et al. ................. 424/484 |
| 2010/0074877 A1 | 3/2010 | Guyonnet et al. ......... 424/93.44 |
| 2010/0098751 A1 | 4/2010 | Dumas et al. ................ 424/450 |
| 2010/0166814 A1 | 7/2010 | Dumas et al. ................ 424/401 |
| 2010/0323045 A1 | 12/2010 | Pischel et al. ................ 424/767 |
| 2011/0052718 A1 | 3/2011 | Rangel .......................... 424/549 |
| 2012/0183627 A1 | 7/2012 | Rizza et al. ................... 424/641 |
| 2012/0308621 A1 | 12/2012 | Novejarque Conde ....... 424/401 |
| 2013/0302389 A1 | 11/2013 | Dumas et al. ................ 424/401 |
| 2014/0004165 A1 | 1/2014 | Novejarque Conde ....... 424/401 |
| 2014/0017341 A1 | 1/2014 | Gourlaouen .................. 424/702 |
| 2015/0147357 A1 | 5/2015 | Gan et al. ................... 424/278.1 |

FOREIGN PATENT DOCUMENTS

| | | |
|---|---|---|
| WO | WO 98/29128 | 7/1998 |
| WO | WO 00/64279 | 11/2000 |
| WO | WO 02/085390 | 10/2002 |
| WO | WO 2007/115840 | 10/2007 |
| WO | WO 2008/043856 | 4/2008 |
| WO | WO 2009/060024 | 5/2009 |
| WO | WO 2009/109946 | 9/2009 |
| WO | WO 2009/138701 | 11/2009 |
| WO | WO 2011/018501 | 2/2011 |
| WO | WO 2011/056549 | 5/2011 |
| WO | WO 2012/052685 | 4/2012 |
| WO | WO 2012/078798 | 6/2012 |
| WO | WO 2013/079394 | 6/2013 |

OTHER PUBLICATIONS

Matias et al., "Antioxidant and Anti-Inflammatory Activity of a Flavonoid-rich Concentrate Recovered from Opuntia Ficus-Indica Juice," *Food and Function*, 2014; 5(12): 3269-3280.

Voronov et al., "IL-1 is Required for Tumor Invasiveness and Angiogensis," *Proceedings of the National Academy of Sciences*, 2003; 100(5): 2645-2650.

* cited by examiner

TOPICAL COSMETIC COMPOSITIONS

CROSS-REFERENCE TO RELATED APPLICATIONS

The present application claims the benefit of U.S. Provisional Application No. 62/269,509, filed Dec. 18, 2015. The contents of the referenced application are incorporated into the present application by reference.

BACKGROUND OF THE INVENTION

A. Field of the Invention

Various skin formulations are disclosed that are structured in such a way to treat a wide range of skin conditions. The formulations can be used separately or in combination in a regimen format to counteract the aging process by using *Opuntia ficus-indica* plant, or an extract thereof, in combination with a cosmetically acceptable vehicle.

B. Description of Related Art

Many factors contribute to skin aging such as the actual age of a person, the amount of exposure to environmental factors (e.g., sun light, pollution, chemicals, smoke, etc.), and how well a person has taken care of their skin. In particular, skin aging concerns two processes—intrinsic aging, which is related to the natural aging process and genetic influences, and extrinsic or accumulated damage due to environmental factors.

Extrinsic factors can include exposure to ultraviolet rays through sun exposure or the use of ultraviolet lamps (for example, tanning beds). Ultraviolet rays can induce oxidative stress and inflammation that leads to skin damage. The accumulation of oxidative stress through free radical formation, can damage skin proteins leading to skin aging, which includes loss of elasticity, loss of dermal proteins, lines and wrinkles, and abnormal pigmentation. Inflammation is also a characteristic of UV and environmental damage. Inflammation can occur through inflammatory cytokines such as tumor necrosis factor alpha (TNF-alpha), vascular endothelial growth factor (VEGF), or enzymes that contribute to the inflammatory pathway such as cyclooxygenase 1, cyclooxygenase 2, and lipoxygenase. As inflammation persists, enzymes such as matrix metalloproteinase-3 (MMP3), and matrix metalloproteinase-9 (MMP9) are involved in the breakdown dermal proteins, which allow immune cells to migrate. This breakdown in dermal proteins such as laminin and collagen can lead to skin aging such as the appearance of fine lines, wrinkles, sagging skin, and loss of skin elasticity.

Furthermore, when exposed to extrinsic factors such the ultra violet (UV) radiation of the sun, irritants, and pollution, the keratinocyte (outermost cell of the skin) releases signaling molecules, such as α-melanocyte-stimulating hormone (α-MSH) and inflammatory cytokines. α-MSH can trigger melanocytes to produce melanin. The production of melanin can result in variations in the color of the skin. For example, a person's skin can have a sallow tone or hyperpigmented or age spots. Conventional depigmenting agents, such as hydroquinone, corticosteroids, and kojic acid can raise several safety concerns (for example, ochronosis, atrophy, carcinogenesis, and other local or systemic side effects) with long-term exposure.

The combination of intrinsic and extrinsic factors eventually leads to visible signs of aging, and over time these signs progress through three stages—early, moderate, and advanced.

The early signs of skin aging include the first stages of visible fine lines, especially around the eyes, and the beginning of uneven skin tone. Cell turnover begins to slow, and this can have a dulling effect on the complexion. Collagen and elastin—while still healthy—can start to suffer early damage, leaving skin slightly less resilient. If the matrix is left unprotected, wrinkles that are forming underneath the surface of the skin will eventually become more noticeable due to damage in the dermal layer. Eyes can occasionally look puffy, and pores appear slightly more noticeable. Typically, this occurs in an age range of about 25 to 35 years of age.

The moderate signs of skin aging include more pronounced expression lines around the eyes, the mouth, and on the forehead. Underneath the eyes dark circles can become more noticeable. The skin's support structure becomes weaker as less collagen is produced, and elastin fibers begin to lose their ability to "snap" back (i.e., loss of skin elasticity). Skin loses vital moisture more easily, and dark spots can become more of an issue. Fine lines on the neck can become more visible, and "marionette" lines on either side of the mouth can begin to appear. More significant age spots begin to surface, eyes may look tired more often, and pores appear larger. This typically occurs in an age range of about 35 to 50 years of age.

The advanced signs of skin aging include "static" deep lines and wrinkles that are visible even when the face is at rest. The supporting structure of collagen and elastin is severely compromised and skin sagging, especially in the cheek and jawline areas, becomes evident. The neck shows signs of cumulative damage, with the skin becoming loose and marked by horizontal wrinkles called "tree rings." Dark spots become more prominent, and the eye area can show noticeable crepiness, sagging, puffiness and more pronounced dark circles in addition to a "drooping" upper eyelid. Skin loses its youthful volume and lift due to a loss of natural cushioning, and skin dryness is more pronounced as the external barrier is compromised, oil production slows, and internal moisture levels drop. Cell turnover slows dramatically, and dead skin cells remain on the skin's surface which can dull the complexion and make pores more noticeable. The thickness of the skin is also impacted, and as it becomes thinner it is more easily irritated. Typically this occurs in an age range of above 50 years of age.

There have been many attempts to solve the problems associated with skin ageing. By way of example, U.S. Pat. No. 6,649,178 to Mohammadi et al. attempts to remedy the effects of stresses of climate extremes with a composition that includes a mixture of botanical ingredients for hot, cold, and dry climate treatment. The hot climate treatment extract is used to impart a cooling effect on the skin. The cold climate treatment extract is used to reduce skin inflammation. The dry climate treatment extract is used to moisturize skin. With respect to the dry climate extract, a number of possible plant extracts are listed, which include extracts of sea pine, prickly pears, orotic acid, hydrolyzed casein, hydrolyzed collagen, hydrolyzed conchorin protein, hydrolyzed corn protein, hydrolyzed elastin, hydrolyzed potato protein, hydrolyzed rice protein, hydrolyzed silk, hydrolyzed soy protein, hydrolyzed wheat protein, phytoglycolipid, millet extract, sigmasterol, sitosterol, soybean sterols, canola derived sterols, campesterol, brassicasterol, and combinations thereof. As another example, U.S. Pat. No. 7,722,904 to Schneider et al. discloses a method for reducing the synthesis of interleukin-1b with Chia seed oil and/or a lipophilic extract from *Opuntia ficus-indica*. However, one of the potential issues with lipophilic extracts is that they are oftentimes difficult to incorporate into aqueous-based compositions, especially those with increased amounts of water (e.g., greater than 50 wt. %) due to the immiscibility of lipophilic and aqueous components. In yet another example, U.S. Pat. No. 8,455,013 to Dumas et al. describes a cosmetic composition that includes extract of nopal as agents for stimulating epidermal kallikreins, which regulate desquamation at the surface of the skin. U.S. Patent Application No. 2014/0004165 to Conde describes a transparent or translucent hypoallergenic and non-irritating base formulation that includes a wide variety of components. The formulation appears to be a non-aqueous base, as the formulation is characterized as having 0 to 7% by weight of water. One of the components in the formulation can be a natural extract such as an extract from the fruit of *Opuntia ficus-indica*. However, no indication of the use or purpose of this extract is mentioned in Conde.

While several of the aforementioned references provide some hope for treating aged skin, they do not appear to effectively address the underlying causes of skin aging.

SUMMARY OF THE INVENTION

The present invention overcomes the aforementioned deficiencies in the art by providing stable cosmetic compositions that can be used for purposes of anti-aging and protection against environmental stressors (e.g., UV light and/or climate). In particular, the solution resides in the discovery that certain extracts of *Opuntia ficus-indica* (e.g., *Opuntia ficus-indica tuna* (prickly pear fruit) and/or *Opuntia ficus-indica nopal* (prickly pear paddles)) can be used to modify specific biochemical pathways that can help address the underlying causes of skin aging. By way of example, it was discovered that extracts of *Opuntia ficus-indica tuna* and/or *nopal*, preferably aqueous extracts of *tuna*, can reduce/inhibit both tumor necrosis factor alpha (TNF-alpha) and vascular endothelial growth factor (VEGF) production in skin cells. TNF-alpha is a pleiotropic cytokine that is believed to play a central role in inflammation in skin cells. VEGF is a cytokine that stimulates vasculogenesis and angiogenesis and is believed to contribute to inflammation in skin cells and ultimately, skin redness (e.g., erythema), and rosacea. Without wishing to be bound by theory, it is believed that by simultaneously attacking both of these biochemical pathways with a single ingredient, the underlying causes of skin aging can be reduced, thereby resulting in skin that has a more youthful appearance. By way of example, it is believed that topical use of the extracts of the present invention can result in skin benefits ranging from improved skin texture and clarity, reduced inflammation of skin, reduced erythema of skin (e.g., reduce the appearance of red discolorations or red blotches), evened out skin tone, reduced fine lines and/or wrinkles, improved overall appearance of the area around the eye, reduced appearance of spider veins (telangiectasia), and/or increased moisture of the skin. It is also believed that alcoholic (e.g., methanol, ethanol, butanol, glycerin, and/or glycolic extracts such as ethylene glycol), aqueous-alcoholic, and even lipophilic extracts of *Opuntia ficus-indica tuna* or *nopales* can be used to reduce TNF-alpha and/or VEGF production in skin cells. The Lipophilic extracts can be prepared by using a lipophilic solvent such as an oil (e.g., plant oil such as sunflower plant oil, preferably sunflower seed oil).

The extracts of the present invention can be used across all skin types (e.g., dry skin, normal skin, oily skin, and combination skin). Such extracts can be beneficial in countering the extrinsic factors of ageing by reducing inflammation through reduction of TNF-alpha production and/or VEGF production. The extract can be beneficial in countering ageing effects caused by inflammation by promoting type I collagen production and inhibiting MMP3 and MMP9 enzyme activities. An increase in type I collagen production can be beneficial in reactivating the production of matrix proteins that are crucial for skin firmness and in reducing the appearance of fine lines, wrinkles, glabellar frowns, crepiness and, thus, enhance skin smoothness. The *Opuntia ficus-indica tuna* and/or *nopal* extract can be mixed with the cosmetically acceptable vehicle to form an oil and water emulsion and/or a serum. The cosmetically acceptable vehicle of the present invention can include water, glycerin, crosslinked polyacrylate polymers, disodium ethylenediaminetetraacetic acid, triethanolamine, polydimethylsiloxane, and polymethyl methylacrylate. In some aspects of the invention, the cosmetic vehicle can include glycerol stearate, cetyl alcohol, cetyl phosphate, cetearyl alcohol, structuring agents, and preservatives. Addition of pentylene glycol, ethylhexyl isononoate, zea mays germ oil, butyrospermum parkii butter, and sucrose polycottonseedate to the topical compositions of the present invention can enhance conditioning of the skin. In other aspects of the present invention, butylene glycol, cyclopentasiloxane, hydrogenated polydecene, caprylyl glycol, squalane, panthenol, polysorbate 20, 1,2-hexanediol, and a copolymer of hydroxymethyl acrylate and acryloyldimethyl taurate can be used when formulating the topical composition as a serum.

In some aspects of the invention, the composition can include at least 50% by weight based on the total weight of the composition (wt. %) of water or 50% to 99.5% wt. % water. The compositions can be formulated as oil-in-water or water-in-oil emulsions, preferably as an oil-in-water emulsion. The composition can be formulated as a serum. The composition can be capable of being applied to the skin and/or the periorbital area of a person's face, and can include the aforementioned *Opuntia ficus-indica tuna* or *nopales* extract and a cosmetically acceptable vehicle. The compositions can include from 0.0001% to 5% by weight, preferably between 0.0001% to 0.5% percent by weight or even 0.0001% to 0.1% by weight of the *Opuntia ficus-indica tuna* and/or *nopales* extract and any combination thereof with the balance being water and/or other ingredients. Methods of applying the oil and water emulsion or serum can include applying any of the oil and water emulsions or serums described throughout this Specification to a portion of a person's face and/or a portion of the periorbital region of a person's face.

In some aspects, the topical skin care composition does not include sea pine, orotic acid, hydrolyzed casein, hydrolyzed collagen, hydrolyzed conchorin protein, hydrolyzed corn protein, hydrolyzed elastin, hydrolyzed potato protein, hydrolyzed rice protein, hydrolyzed silk, hydrolyzed soy protein, hydrolyzed wheat protein, phytoglycolipid, millet extract, sigmasterol, sitosterol, soybean sterols, canola derived sterols, campesterol, and/or brassicasterol. In some instances, the compositions do not include trehalose, aloe extract, guava, hydroxy-alpha-sanshool, hydroxy-beta-sanshool, hydroxy-gamma-sanshool, menthol, anethole, isopulegol, menthoxypropane-1,2,diol,menthone,menthyl acetate, eucalyptol, methyl salicylate, N-2,3-trimethyl-2-isopropylbutanamide, N-ethyl-p-menthane-3-carboxamide, menthyl lactate, menthyl succinate, menthone glycerol ketal spilanthol, N-acetyl glycine menthyl ester, L-menthol-3-hydroxybutyrate, 2-isopropenyl-1-methylcyclohexanol, trialkyl-substituted cyclohexane carboxamides, cyclohexanamides, N-ethyl-p-methane-3-carboxamide, 2-mercaptocyclo-decanone, 2-isopropanyl-5-methylcyclohexanol and mixtures thereof. In some aspects, the compositions do not include a hydrocarbon (e.g., mineral oil, terpenes, isoparraffins, polyethylene waxes, petroleum jelly). In yet other instances, the compositions do not include a silicone fluid nor a $C_6$-$C_{40}$ ester. In further aspects, the compositions of the present invention do not include chia seed oil and/or an extract of common mallow (*Malva sylvestris*). In yet further embodiments, the compositions of the present invention do not include a hydroxylated ester, a mineral oil, at least one copolymer derived from alkenes, a hydrogenated polymer, and/or a glyceryl glucoside.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, a skin lightening ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also disclosed are methods of treating erythema, inflammation, rosacea, and/or psoriasis that include topically applying any of the compositions of the present invention to skin in need thereof, wherein said composition inhibits/reduces VEGF, or TNF-alpha. In some aspects, said compositions are applied to red blotches on skin.

In a further embodiment, there is disclosed a method of treating spider veins (telangiectasia). The method can include topically applying any of the compositions of the present invention to skin in need thereof (i.e., applied to skin having or susceptible of developing spider veins), wherein said composition inhibits/reduces VEGF or TNF-alpha production in skin and reduces the appearance of spider veins. In particular, reducing VEGF production is believed to reduce vasculogenesis and/or angiogenesis, thereby reducing the appearance of spider veins.

Kits that include the compositions of the present invention are also contemplated. In certain embodiments, the composition is comprised in a container. The container can be a bottle, dispenser, or package. The container can dispense a pre-determined amount of the composition. In certain aspects, the compositions are dispensed in a spray, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse of composition can be a skin cleanser, shampoo, conditioner, or soap. An example of a leave-on composition can be a skin moisturizer, sunscreen, mask, overnight cream, serum or a day cream. Also contemplated is a product that includes a lipstick, a toner, a sunscreen, a mask, an anti-aging product, a deodorant, an antiperspirant, a perfume, a cologne, etc.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "weight percent," "wt. %," "volume percent," or "vol. %" refers to a weight or volume percentage of a component, respectively, based on the total weight or the total volume of material that includes the component. In a non-limiting example, 10 grams of component (e.g., *Opuntia ficus-indica* fruit or *nopales* extract) in 100 grams of the material (topical skin composition) is 10 wt. % of component.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the *Opuntia ficus-indica* extracts of the present invention (e.g., *Opuntia ficus-indica tuna* (prickly pear fruit) and/or *Opuntia ficus-indica nopal* (prickly pear paddles)) are their ability to reduce TNF-alpha and/or vascular endothelial growth factor (VEGF) production in skin cells.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Given the number of various products on the market today and the myriad of different skin types, a person is oftentimes at a loss to identify an appropriate product to help counteract the intrinsic and extrinsic factors that contribute to the aging process.

The cosmetic compositions and formulations of the present invention can be used to counteract the factors contributing to the aging process and maintain and improve the health of a variety of skin types. The compositions can include *Opuntia ficus-indica* extract(s) (e.g., *Opuntia ficus-indica tuna* (prickly pear fruit) and/or *Opuntia ficus-indica nopal* (prickly pear paddles)), which have the ability to reduce TNF-alpha and/or vascular endothelial growth factor (VEGF) production in skin cells. By down regulating these biochemical pathways associated with inflammation in skin cells, it is believed that positive benefits for the skin can result. Non-limiting examples of such positive benefits include counteracting oxidative and inflammatory damage in skin cells, increasing dermal proteins such as collagen and laminin in skin cells, reducing pigmentation in skin cells, and/or reduce lipid peroxides and protein oxidation in skin cells. This can result in skin having a more youthful appearance such as improved skin texture and clarity, reduced inflammation of skin, reduced erythema of skin (e.g., reduce the appearance of red discolorations or red blotches), evened out skin tone, reduced fine lines and/or wrinkles, improved overall appearance of the area around the eye, reduced appearance of spider veins (telangiectasia), and/or increased moisture of the skin.

These and other non-limiting aspects of the present invention are provided in the following subsections.

A. *Opuntia Ficus-Indica* Plant and Extracts Thereof

The present invention is premised on the discovery that the active ingredients found in extracts of the *Opuntia ficus-indica* plant including extracts of *Opuntia ficus-indica tuna* and/or extracts of *Opuntia ficus-indica nopal* can be used to improve the improve the skin's visual appearance, counteract the extrinsic and intrinsic effects of aging, treat erythema, inflammation, rosacea, psoriasis, or related disorders, and even out a person's skin tone (e.g., even out the color of skin). This active ingredient can be used in different products (e.g., a day cream, an eye cream, and a serum) to treat various skin conditions. By way of example, a day cream can help moisturize skin and help lessen reddening of the skin. An eye cream can help firm up skin and increase microcirculation to reduce the appearance of under eye bags while also reducing the appearance of dark circles. A serum can have a concentrated amount of these ingredients to help reduce the accumulation of proteins that can lead to skin aging or inflammation.

The compositions and formulation of the present invention can be particularly beneficial for skin that has begun to develop lines, wrinkles and/or crepiness. In addition to counteracting the aging process, the combination of ingredients hydrates and brightens the skin and protects skin form environmental damage.

Also commonly known as prickly pear, *Opuntia tuna* is the fruit and *Opuntia nopal* is the paddle of a family of cactus native to the Americas. The whole prickly pear plant or fruit and/or paddles are typically extracted using a maceration process with organic oils/solvents and/or aqueous solvents. In non-limiting instances, the extracts can be obtained by using the extraction processes illustrated in Example 1. By way of example, the plant can be macerated and then be subjected to an extraction solvent/extractant and collected. Insoluble materials and particulates can be filtered out to obtain the solvent. In some instances, the extractant can be water or alcohol or a combination thereof (i.e., aqueous-alcoholic mixture). The alcohol can be methanol, ethanol, glycerin, or a glycol (e.g., ethylene glycol). Alternatively, the extractant can be an oil such as a plant oil or a vegetable oil. A non-limiting plant oil can be oil from the sunflower plant (e.g., sunflower seed oil). The aqueous, alcoholic, aqueous-alcoholic, and oil extracts can include ingredients that are soluble in the extractant that was used.

B. Cosmetic Vehicle

The cosmetic vehicle of the present invention has been designed to work for all skin types (e.g., oily, dry, or combination) and all age ranges. The cosmetic vehicle can be formulated as a skin cream, an eye cream, or a serum. Non-limiting examples of the cosmetic vehicle include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

In one instance, the cosmetic vehicle can include 50 to 70% water, 1 to 3% by weight polydimethylsiloxane, 1 to 12% by weight of glycerin, 0.01 to 0.3% by weight cross-linked polyacrylate polymers, 0.01 to 0.2% by weight disodium EDTA, 0.01 to 1% by weight triethanolamine, and 0.01 to 1% by weight polymethyl methylacrylate 1 to 5% by weight pentylene glycol, 1 to 5% by weight glyceryl stearate, 1 to 5% by weight ethylhexyl isononoate, 1 to 3% by weight cetyl alcohol, 1 to 5% by weight butyrospermum parkii butter, 1 to 3% by weight cetyl phosphate, 1 to 3% by weight cetearyl alcohol, 0.01 to 1% by weight sucrose polycottonseedate, 0.01 to 1% by weight structuring agents, and 0.01 to 0.5% by weight preservatives. In another instance, the cosmetic vehicle can include 60 to 70% water, 1 to 12% by weight of glycerin, 0.01 to 0.3% by weight crosslinked polyacrylate polymers, 0.01 to 0.2% by weight disodium ethylenediaminetetraacetic acid (EDTA), 0.01 to 1% by weight triethanolamine, and 0.01 to 1% by weight polymethyl methylacrylate. In some embodiments, the serum can include 60 to 70% water, butylene glycol, cyclopentasiloxane, hydrogenated polydecene, caprylyl glycol, squalane, panthenol, polysorbate 20, 1,2-hexanediol, and a copolymer of hydroxymethyl acrylate and acryloyldimethyl taurate, 1 to 7% by weight butylene glycol, 1 to 7% by weight cyclopentasiloxane, 1 to 5% by weight hydrogenated polydecene, 0.01 to 1% by weight caprylyl glycol, 0.01 to 1% by weight squalane, 0.01 to 1% by weight panthenol, 0.01 to 1% by weight polysorbate 20, 0.01 to 0.5% by weight 1,2-hexanediol, and 0.01 to 0.5% by weight a copolymer of hydroxymethyl acrylate and acryloyldimethyl taurate.

C. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

D. Additional Ingredients

In addition to the active ingredients and cosmetic vehicles, the compositions can also include additional ingredients such as cosmetic ingredients and other pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D & C blue no. 4, D & C green no. 5, D & C orange no. 4, D & C red no. 17, D & C red no. 33, D & C violet no. 2, D & C yellow no. 10, and D & C yellow no. 11), adsorbents, lubricants, solvents, moisturizers (including, e.g., emollients, humectants, film formers, occlusive agents, and agents that affect the natural moisturizing mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. *aloe vera*, chamomile, cucumber extract, *ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, and mannitol), exfoliants, emulsifier stabilizers (e.g., hydroxypropyl cyclodextrin), waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetra sulfonate, diethyl amino hydroxybenzoyl hexyl benzoate, bis-diethyl amino hydroxybenzoyl benzoate, bis benzoxazoylphenyl ethylhexylimino-triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl-4-methoxycinnamate. Non-limiting examples of physical sun blocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *aloe barbadensis*, *aloe-barbadensis* extract, *aloe barbadensis* gel, *althea officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamom (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythritol hexacaprylate/hexacaprate, DNA, erythritol, ethoxydiglycol, ethyl linoleate, eucalyptus globulus oil, evening primrose (*oenothera biennis*) oil, fatty acids, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica* limonum) oil, linoleic acid, linolenic acid, *macadamia ternifolia* nut oil, maltitol, *matricaria* (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil is derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners include those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyl-taurate/vp copolymer, or a mixture thereof.

Non-limiting examples of additional thickening agents that can be used in the context of the present invention include carboxylic acid polymers, cross-linked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid cross-linked with allyl ethers of sucrose or pentaerythritol (e.g., Carbopol™ 900 series from B. F. Goodrich).

Non-limiting examples of cross-linked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, iso-paraffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propyl parabens), phenoxy ethanol, benzyl alcohol, chlorobutanol, phenol, sorbic acid and salts thereof, thimerosal, potassium sorbate, or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti-seborrheic agents, biologically active proteins and peptides, burn treatment agents, cauterizing agents, depigmenting agents, depilatories, diaper rash treatment agents, enzymes, hair growth stimulants, hair growth retardants including difluoromethylonithine (DFMO) and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

E. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions. In one instance, a composition of the present invention can be comprised in a plastic container capable of holding the composition and expelling the composition from the container. The plastic can be comprised of a thermoset and/or a thermoplastic polymer.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Manufacturing Procedure

Prickly pear extracts used throughout the Examples were manufactured by a maceration process at Carrubba Inc. (Milford, Conn., USA). The process uses the selected plant or plant part (e.g., whole prickly pear plant (*Opuntia ficus-indica*) or fruit (*Opuntia ficus-indica tuna*), paddles (*Opuntia ficus-indica nopales*)). The plant used was sourced from Mexico. Oil-based and aqueous-based extracts of the plant or plant part were prepared as follows. For oil extracts, the whole plant or plant part (e.g., fruit and/or paddles) is placed in a tank holding sunflower oil and macerated. Upon completion of the extraction process, the extract was filtered.

For aqueous extracts, the whole plant or plant part (e.g., fruit and/or paddles) is placed in a tank holding water and macerated. Glycerin and preservatives held in a separate tank were then mixed with the macerated whole prickly pear plant or fruit and/or paddles.

Formulations having the ingredients from Example 1 were prepared as topical skin or hair compositions.

Example 2

Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Cytokin Tumor Necrosis Factor Alpha (TNF-α) Assay: Aqueous *Opuntia ficus-indica tuna* extract from Example 1 has been shown to inhibit TNF-α production by about 89% at 1% concentration and 51.9% at a 0.01% concentration. The prototype ligand of the TNF superfamily, TNF-α, is a pleiotropic cytokine that plays a central role in inflammation. Increase in its expression is associated with an up regulation in pro-inflammatory activity.

The bioassay used to assess the TNF-alpha inhibition properties of aqueous *Opuntia ficus-indica tuna* extract from Example 1 is designed to analyze the effect of the extract on the production of TNF-α by human epidermal keratinocytes. The endpoint of this assay is a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples are pipetted into the wells and any TNF-α present is bound by the immobilized antibody. After washing away any unbound substances, an enzyme-linked polyclonal antibody specific for TNF-α is added to the wells. Following a wash to remove any unbound antibody-enzyme reagent, a substrate solution is added to the wells and color develops in proportion to the amount of TNF-α bound in the initial step using a microplate reader for detection at 450 nm. The color development is stopped and the intensity of the color is measured. Subconfluent normal human adult keratinocytes (Cascade Biologics) cultivated in EpiLife standard growth medium (Cascade Biologics) at 37° C. in 5% $CO_2$, are treated with phorbol 12-myristate 13-acetate (PMA, 10 ng/ml, Sigma Chemical, #P1585-1MG) and the extract for 6 hours. PMA has been shown to cause a dramatic increase in TNF-α secretion which peaks at 6 hours after treatment. Following incubation, cell culture medium is collected and the amount of TNF-alpha secretion is quantified using a sandwich enzyme linked immuno-sorbant assay (ELISA) from R & D Systems (#DTA00C).

Cytokine array (includes VEGF): Aqueous *Opuntia ficus-indica tuna* extract from Example 1 has been shown to inhibit VEGF production. VEGF is a cytokine that stimulates vasculogenesis and angiogenesis and may contribute to inflammation, redness, and rosacea. Aqueous *Opuntia ficus-indica tuna* extract inhibition of VEGF production was determined with a protein detection assay using biotinylated antibodies to a variety of cytokines for detection of the antibodies. It was determined that aqueous *Opuntia ficus-indica tuna* extract inhibits VEGF production by about 82% at a 1% concentration and about 43.6% at a 0.1% concentration.

Briefly, human epidermal keratinocytes were cultured to 70-80% confluency. The media in the plate was aspirated and 0.025% trypsin/EDTA was added. When the cells became rounded, the culture dish was gently tapped to release the cells. The trypsin/EDTA containing cells were removed from the culture dish and neutralized. Cells were centrifuged for 5 min. at 180×g. The cells formed a pellet and the supernatant was aspirated. The resulting pellet was resuspended in EpiLife™ media (Cascade Biologics). The cells were seeded in 6-well plates at approximately 10-20% confluency. After the cells became approximately 80% confluent, the media was aspirated and 1.0 ml of EpiLife™, along with phorbol 13-Myristate 12-acetate ("PMA") (a known inducer of inflammation) and the test composition dilutions were added to two replicate wells (i.e., 1.0% (100 µl of 100× stock) and 0.1% (10 µl of 100× stock) test compositions were diluted into a final volume of 1 ml EpiLife Growth Medium). The media was gently swirled to ensure adequate mixing. In addition, 1.0 ml of EpiLife™ was added to the control wells, with and without additional PMA. The plates were then incubated at 37±1° C. and 5.0±1% $CO_2$ for approximately 5 hours after dosing. Following this 5-hour incubation, all media was collected in conical tubes and frozen at −70° C. and the frozen media was subsequently shipped on dry ice.

On the day of the analysis, a 16-pad hybridization chamber was attached to 16-pad FAST slides arrayed in triplicate with 16 anti-cytokine antibodies (including VEGF) plus experimental controls (Whatman BioSciences), and the slides were placed into a FASTFrame (4 slides per frame) for processing. Arrays were blocked for 15 min. at room temp. using 70 ml S & S Protein Array Blocking buffer (Whatman Schleicher and Scheull). Blocking buffer was removed and 70 ml of each supernatant sample was added to each array. Arrays were incubated for 3 hours at room temp. with gentle agitation. Arrays were washed 3 times with TBS-T. Arrays were treated with 70 ml of an antibody cocktail, containing one biotinylated antibody corresponding to each of the arrayed capture antibodies. Arrays were incubated for 1 hour at room temp. with gentle agitation. Arrays were washed 3 times with TBS-T. Arrays were incubated with 70 ml of a solution containing streptavidin-Cy5 conjugate for 1 hour at room temp. with gentle agitation. Arrays were washed 3 times with TBS-T, quickly rinsed in de-ionized water, and dried.

Slides were imaged in a Perkin-Elmer ScanArray 4000 confocal fluorescent imaging system. Array images were saved and analyzed using Imaging Research ArrayVision software. Briefly, spot intensities were determined by subtracting background signal. Spot replicates from each sample condition were averaged and then compared to the appropriate controls.

Example 3

Other Assays

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified.

Collagen Stimulation Assay: Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Antioxidant (AO) Assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®.+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit # 709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®.+ by metmyoglobin. The capacity of the antioxidants in the sample to prevent ABTS oxidation can be compared with that Trolox, a water-soluble tocopherol analogue, and was quantified as a molar Trolox equivalent.

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\epsilon$=13,600 M-1 cm−1 at pH 6.0 and above 7). The active ingredients, any one of the combination of ingredients, or compositions having said combinations disclosed in the specification can be assayed.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression was evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay: EnzChek® Elastase Assay (Kit# E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin.

This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification compositions can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of treating inflamed skin by reducing tumor necrosis factor alpha (TNF-α) or vascular endothelial growth factor (VEGF) production in skin cells, the method comprising topically applying to inflamed skin, a composition comprising 0.01 wt. % to 0.5 wt. % of an aqueous extract of *Opuntia ficus-indica tuna, Opuntia ficus-indica nopales*, or a combination thereof to reduce TNF-α or VEGF production in skin cells to treat the inflamed skin, wherein the composition further comprises at least 50 wt. % water.

2. The method of claim 1, wherein the composition comprises an aqueous extract of *Opuntia ficus-indica tuna*.

3. The method of claim 2, wherein the composition is applied to erythemic skin.

4. The method of claim 2, wherein the composition is applied to a fine line or wrinkle.

5. The method of claim 2, wherein the composition is applied to the periorbital area of a person's face.

6. The method of claim 1, wherein the composition is applied to rosacea or psoriasis.

7. The method of claim 1, wherein the composition does not include a hydrocarbon, a silicone fluid, an organic sunscreen, chia seed oil, an extract of common mallow, a hydrogenated polymer, and a glyceryl glucoside.

8. The method of claim 1, wherein the composition comprises 0.01 wt. % to 0.1 wt. % of the *Opuntia ficus-indica tuna, Opuntia ficus-indica nopales*,or both, or extracts thereof.

9. The method of claim 1, wherein the composition comprises an effective amount of an aqueous extract of *Opuntia ficus-indica nopal*.

10. The method of claim 1, wherein the composition is formulated as a serum comprising 60 to 70 wt. % water, and further comprises:
butylene glycol;
cyclopentasiloxane;
hydrogenated polydecene;
dimethicone/vinyl dimethicone cross polymer;
capryl glycol;
1,2-hexanediol;
hydroxyethyl acrylate/sodium acryloyldimethyl taurate copolymer;
polysorbate 20;
squalane; and
-panthenol.

11. The method of claim 1, wherein the composition is formulated as a serum and further comprises:
water;
glycerin;
acrylates/$C_{10-30}$ alkyl acrylate crosspolymer;
disodium ethylenediaminetetraacetic acid;
triethanolamine;
polydimethylsiloxane;
polymethyl methylacrylate;
glyceryl stearate;
pentylene glycol;
ethylhexyl isononanoate;
cetyl alcohol;
butyrosperum parkii butter;
zea mays germ oil;
cetyl phosphate;
cetearyl alcohol; and
ceteareth-33.

* * * * *